(12) United States Patent
Burns et al.

(10) Patent No.: US 12,064,376 B2
(45) Date of Patent: Aug. 20, 2024

(54) RHO KINASE INHIBITOR RELEASING IMPLANTS AND RELATED METHODS OF USE

(71) Applicant: Glaukos Corporation, San Clemente, CA (US)

(72) Inventors: Tom Burns, San Juan Capistrano, CA (US); Jia-Ying Yang, Mission Viejo, CA (US); Patrick Michael Hughes, Aliso Viejo, CA (US)

(73) Assignee: GLAUKOS CORPORATION, San Clemente, CA (US)

( * ) Notice: Subject to any disclaimer, the term of this patent is extended or adjusted under 35 U.S.C. 154(b) by 207 days.

(21) Appl. No.: 17/336,789

(22) Filed: Jun. 2, 2021

(65) Prior Publication Data

US 2021/0378862 A1   Dec. 9, 2021

Related U.S. Application Data

(60) Provisional application No. 63/034,273, filed on Jun. 3, 2020.

(51) Int. Cl.
| | | |
|---|---|---|
| *A61F 9/00* | (2006.01) | |
| *A61L 27/18* | (2006.01) | |
| *A61L 27/34* | (2006.01) | |
| *A61L 27/54* | (2006.01) | |
| *A61L 27/58* | (2006.01) | |
| *C08L 23/08* | (2006.01) | |
| *C08L 67/04* | (2006.01) | |
| *C08L 83/08* | (2006.01) | |

(52) U.S. Cl.
CPC ............ *A61F 9/0017* (2013.01); *A61L 27/18* (2013.01); *A61L 27/34* (2013.01); *A61L 27/54* (2013.01); *A61L 27/58* (2013.01); *C08L 23/0853* (2013.01); *C08L 67/04* (2013.01); *C08L 83/08* (2013.01); *A61F 2210/0004* (2013.01); *A61F 2210/0076* (2013.01); *A61F 2220/0016* (2013.01); *A61F 2250/0067* (2013.01); *A61L 2300/204* (2013.01); *A61L 2300/432* (2013.01); *A61L 2300/604* (2013.01); *A61L 2300/62* (2013.01); *C08L 2201/06* (2013.01); *C08L 2203/02* (2013.01)

(58) Field of Classification Search
None
See application file for complete search history.

(56) References Cited

U.S. PATENT DOCUMENTS

2007/0149548 A1 *   6/2007   Hellberg ............ A61K 31/497
                                                              514/573
2008/0292679 A1    11/2008   Lyons et al.
(Continued)

OTHER PUBLICATIONS

International Search Report and Written Opinion dated Sep. 15, 2021 for international application PCT/US2021/035431.

*Primary Examiner* — Dominic Lazaro
(74) *Attorney, Agent, or Firm* — Stoel Rives LLP

(57) ABSTRACT

The present disclosure is directed to intracameral implants for treating and/or preventing corneal disorders, diseases, and/or conditions, such as corneal endothelial dystrophies. The intracameral implants can be configured to provide a sustained release of a therapeutic agent, such as a Rho kinase inhibitor, for a prolonged period of time. The intracameral implants can include a non-bioresorbable anchor or a bioresorbable matrix.

12 Claims, 2 Drawing Sheets

(56) References Cited

U.S. PATENT DOCUMENTS

| | | | |
|---|---|---|---|
| 2010/0247606 A1* | 9/2010 | Robinson | A61K 31/557 514/369 |
| 2015/0104491 A1* | 4/2015 | Shi | A61K 31/382 424/428 |
| 2018/0296474 A1 | 10/2018 | Behar-Cohen et al. | |
| 2018/0369017 A1 | 12/2018 | Scheiber et al. | |
| 2019/0307551 A1 | 10/2019 | Peyman | |

* cited by examiner

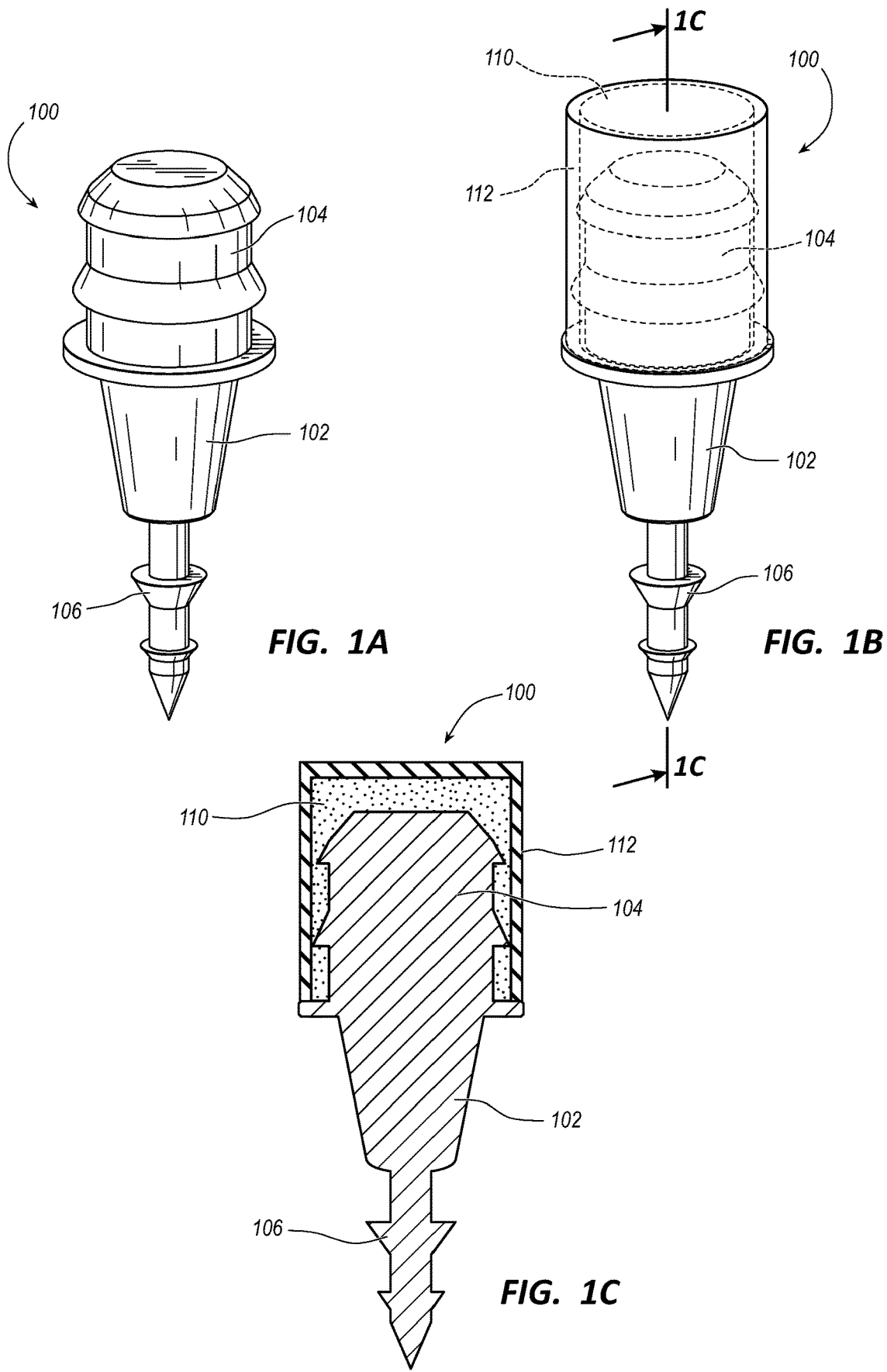

RHO KINASE INHIBITOR RELEASING IMPLANTS AND RELATED METHODS OF USE

CROSS-REFERENCE TO RELATED APPLICATIONS

This application claims priority to U.S. Provisional Application No. 63/034,273, filed Jun. 3, 2020, and titled RHO KINASE INHIBITOR RELEASING IMPLANTS AND RELATED METHODS OF USE, which is hereby incorporated by reference in its entirety.

TECHNICAL FIELD

The present disclosure relates to intracameral implants for treating and/or preventing corneal disorders, diseases, and/or conditions, such as corneal endothelial dystrophies. Methods of making and/or using the implants are also disclosed.

BRIEF DESCRIPTION OF THE DRAWINGS

The written disclosure herein describes illustrative embodiments that are non-limiting and non-exhaustive. Reference is made to certain of such illustrative embodiments that are depicted in the figures, in which:

FIG. 1A is a perspective view of an implant, according to one embodiment of the present disclosure;

FIG. 1B is a perspective view of the implant of FIG. 1A, which includes a therapeutic composition disposed on the implant;

FIG. 1C is a cross-sectional view of the implant of FIG. 1B, taken along the view line 1C-1C;

DETAILED DESCRIPTION

Figure 2A:
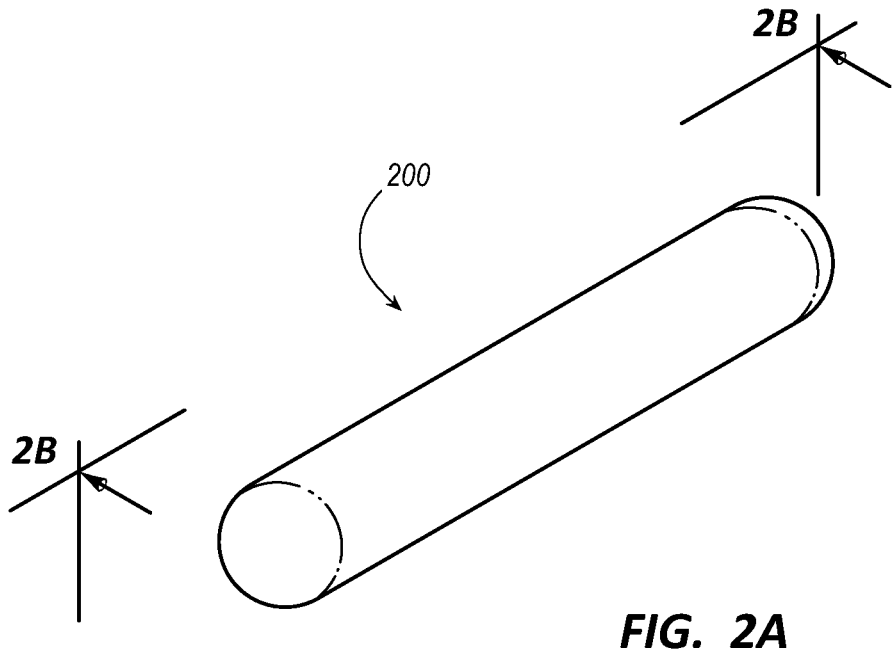
FIG. 2A is a perspective view of an implant, according to another embodiment of the present disclosure.

Rho kinase (ROCK), also known as Rho-associated protein kinase, is a serine-threonine protein kinase. ROCK is a downstream effector of RhoA, a GPTase. ROCK typically occurs within mammals in two (2) isoforms: ROCK1 and ROCK2. Various substrates can be phosphorylated by ROCKs. For instance, ROCK can phosphorylate myocin light chain phosphatases and cause accumulation of phosphorylated myosin. ROCKs can also act to directly phosphorylate myosin light chains. This phosphorylation, in addition to the action of ROCK on RhoA CPI-17 and LIM-1 and LIM-2 kinases, can result in the assembly and/or stabilization of actin fibers and/or filaments. This assembly and stabilization of actin fibers and/or filaments can regulate cellular focal adhesion, contraction, migration, and proliferation. ROCKs can also act via ICAM-1 (intracellular adhesion molecule-1) and may inhibit nitric oxide (NO) levels via inhibition of nitric oxide synthase.

ROCK has been shown to be expressed in the human cornea. Cell culture, in vivo animal studies, and small case studies in humans have also shown that topical ophthalmic administration of Rho kinase inhibitors (ROCK inhibitors) can be beneficial to the treatment and prevention of corneal disorders, diseases, and/or conditions, such as corneal endothelial dystrophies.

For instance, the effects of ROCK inhibitors on corneal endothelial cells in animal models have been studied in vitro and in vivo. Okumura (Okumura N, Okazaki Y. Inoue R.; Effect of the Rho-Associated Kinase Inhibitor Eye Drop (Ripasudil) on Corneal Endothelial Wound Healing. Invest Ophthalmol Vis Sci 2016) assessed the effects of ROCK inhibitors on human corneal endothelial cells (HCEC) in vitro as well as in a rabbit corneal endothelial damage model. In vitro, HCECs were seeded on a culture plate for 24 hours and then treated with a ROCK inhibitor (0.3 to 100 µM ripasudil, 10 µM Y-27632, or 10 µM fasudil) for 48 hours. DNA and endothelial cell proliferation was significantly enhanced with the ROCK inhibitor ripasudil 0.3 to 30 µM.

The effect of the ROCK inhibitor ripasudil on an in vivo rabbit corneal endothelial damage model was also assessed by slit lamp, BrdU, Ki67, and Na/K ATPase. In doing so, a freeze model and a scrape model were utilized. Topical 0.4% or 0.8% ripasudil drops were then administered BID or QID, respectively. For the freeze model, the wound was smaller in ROCK inhibitor treated eyes and less hazy corneas were observed versus controls. Proliferation was better in the ROCK inhibitor treated eyes in a dose dependent fashion. In the scrape model at day 14, the ripasudil treated eyes were clear (5/6) whereas 0/6 of the control group were clear. Corneal thickening was deceased to ⅓ with ripasudil and no change with control.

Meekins (Meekins L. Rosado-Adames N. Maddala R., Corneal Endothelial Cell (CECs) Migration and Proliferation Enhanced by Rho Kinase (ROCK) Inhibitors in In Vitro and In Vivo Models. Invest Ophthalmol Vis Sci 2016) evaluated the ROCK inhibitors Y-27632 and H-1152 on porcine cell proliferation in vitro. Porcine corneal endothelial cells (CECs) were grown to confluence and scratched. 10 µM Y-27632 or 2.5 µM H-1152 were incubated for 2, 24 and 48 hours. Cells initially grew to a monolayer and those treated with a ROCK inhibitor showed a monolayer with polygonal structure and tight junctions. Migration of cells from the scratch was enhanced with the ROCK inhibitors. In the rabbit model of corneal endothelial dysfunction, topical drops of 1 mM H-1152 were given as 2 drops QID for three days, then TID for seven days were given to assess effect. Corneal thickness in rabbits was less in H-1152 treated animals than in controls.

Okumura (Okumura N. Sakamoto Y. Fujii K., Rho Kinase Inhibitor Enables Cell-Based Therapy for Corneal Endothelial Dysfunction, Nature 2016) demonstrated that corneal endothelial cells could be successfully grafted to decompensated monkey corneas when supplemented with the ROCK inhibitor Y-27632. A monkey model of corneal endothelial cell damage was created by scrapping the corneal endothelium completely from the Descemet's membrane of cynomolgus monkeys using a 20-gauge silicone needle. Monkey CECs (MCEC) were administered with concomitant ROCK inhibitor as an 100 intracameral injection regenerated without adverse events such as glaucoma. The $5\times10^5$ CECs were injected in 200 µl with µM ROCK inhibitor into the primate. Primates were placed face down for 3 hours. The ROCK inhibitor enhanced the survival and engraftment of injected cultured endothelial cells. Primate CECs administered without ROCK inhibitor were not effectively engrafted. At 1 year, MCEC and ROCK inhibitor eyes demonstrated clear corneas with 2000 cells/mm$^2$. Cells with ROCK were monolayered and hexagonal. MCEC without ROCK was hazy.

Clinical effects of ROCK inhibitors on corneal endothelial cells has also been shown. The corneal endothelium normally has a cell density of between about 2500 and 3000 cells/mm$^2$. Without being bound by any particular theory, anything less than about 500 to 1000 cells/mm$^2$ depending on source, can lead to decompensation (e.g., edema and hazing).

ROCK inhibitor Y-27632 was shown to be effective in Fuch's corneal dystrophy in preserving corneal clarity (Okumura N, Koizumi N, Kay E P, et al. The ROCK Inhibitor Eye Drop Accelerates Corneal Endothelium Wound Healing. IOVS 2013). This was effective in mild cases (central edema) of corneal endothelial dysfunction, but not severe (diffuse edema) indicating treating early or prophylaxis would be good. Some healthy CEC was necessary. Corneas returned to clarity in 1 to 2 months for ROCK topical treated decompensated corneas. Y-27632 was shown to decrease corneal thickening in Fuch's patients.

Okumura (N. Okumura, R. Inoue, Y. Okazaki et al., Effect of the Rho Kinase Inhibitor Y-27632 on Corneal Endothelial Wound Healing, IOVS 2015) treated three patients with severe corneal edema and corneal hazing. The injuries were the result of cataract surgery. A topical dose of 1 mM Y-27632 was given by topical eye drop six times daily for 4 months, followed by four times daily for 2 additional months. Corneal transparency was recovered in 1 to 2 months. In another case study the ROCK inhibitor ripasudil salvaged patient with failed descemetorhexis.

In September 2019, Kowa submitted an Investigational New Drug Application to the U.S. Food and Drug Administration to begin Phase 2 Study of the ROCK inhibitor ripasudil hydrochloride hydrate. Kowa will investigate the efficacy and safety in patients with corneal endothelial diseases.

Kinoshita et al. (Kinoshita S, Koizumi N.; Ueno M., Injection of Cultured Cells with a ROCK Inhibitor for Bullous Keratopathy, N. Engl J. Med 2018) studied ROCK inhibitor Y-27632 injection with cultured human CECs in patients with bullous keratopathy. Eleven patients were studied, but as of 2018 a total of 33 patients have undergone the procedure. The patients had decompensated corneas with no detectable CECs. Then human CECs were cultured and injected into the patients at 1×10$^6$ cells per 300 μL with Y-27632 added to the medium. The patients were then laid prone, face down for three hours to facilitate engraftment. The primary endpoint was clearing of cornea and CEC>500 mm$^2$. The secondary endpoints include corneal thickness and BCVA. By 24 weeks 11 had >500 cells/mm$^2$ and 10 had >1000 cells/mm$^2$. Corneas became clear and <630 μm in all but 1 case. One case of steroid induced intraocular pressure (IOP) and no other adverse events.

It is thus believed that ROCK inhibitors can be beneficial in the treatment and prevention of corneal disorders, diseases, and/or conditions. Topical administration of ROCK inhibitors has also been shown to mitigate corneal endothelial dystrophies in cell culture, animal models, and in humans. However, the concentrations shown to be effective are often in the range of 0.3 μM to 30 μM. This is on the order of 10 ng/mL to 1000 ng/m L. And typical concentrations achieved after topical dosing of a ROCK inhibitor are often on the order of 5 ng/mL, the low end of the effective range.

Topical dosing in human clinical studies evaluating the effect of ROCK inhibitors on corneal endothelial dystrophies has required QID to six times a day dosing often for weeks or months. A Phase 2 clinical study was initiated in 2019 sponsored by Lions Vision Gift Research and the Eye Bank Association of America evaluating the efficacy of the ROCK inhibitor ripasudil 0.4% eye drops after descemetorhexis in patients with moderate to advanced Fuch's endothelial corneal dystrophy. Ripasudil eye drops are being administered six times per day for 2-4 weeks. Okumura (Okumura, IOVS 2015) treated three patients with severe corneal edema and corneal hazing. The injuries were the result of cataract surgery. A topical dose of 1 mM of the ROCK inhibitor Y-27632 was given by topical eye drop six times daily for four months, followed by four times daily for two additional months.

Topical administration can thus be difficult. For example, topical ophthalmic dosing of medications often requires a high dose due to the low bioavailability of most topically applied drugs. Typically, only 1% to 5% of a topically administered small molecule eye drop is bioavailable to the aqueous humor. This can result in a pulsed dosing of the drug to the surface of the eye with very high concentrations, which can lead to side effects such as hyperemia and chemosis in the case of dosing ROCK inhibitors. Hence, achieving a sustained >5 ng/mL to 10,000 ng/mL therapeutic concentration is difficult with topical dosing.

The present disclosure is directed towards the delivery of ROCK inhibitors via an intracameral implant. The implants can achieve a sustained delivery of ROCK inhibitors to the eye, and can be useful in the treatment and prevention of corneal disorders, diseases, and/or conditions, such as corneal endothelial dystrophies. In some embodiments, the implants can be useful for the treatment or prevention of corneal disorders, diseases, and/or conditions (such as corneal endothelial dystrophies) that result from one or more of ocular surgery, cataract surgery, insertion of an implant, Fuch's corneal dystrophy, and failed descemetorhexis. Thus, it will be appreciated that the implants disclosed herein can be used to treat corneal endothelial cell (CEC) damage that is the result of a disease (e.g. Fuchs' corneal dystrophy) or that is the result of an iatrogenic condition, such as damage during a surgery (e.g., ocular surgery, cataract surgery, insertion of an implant, and/or failed descemetorhexis).

In some embodiments, the implants are inserted, implanted, or otherwise disposed into the aqueous humor of a patient. Once implanted, the implants can deliver ROCK inhibitors directly to the intracameral space such that the therapeutic effect of the ROCK inhibitor is maintained over a prolonged period of time, such as least one week, two weeks, three weeks, four weeks or longer. For instance, the implants can deliver a ROCK inhibitor at a rate sufficient to create a steady state aqueous humor concentration of ROCK inhibitor of between about 0.001 μM to about 100 μM for the prolonged period of time (e.g., as least one week, two weeks, three weeks, four weeks or longer). In another embodiment, the implants can deliver a ROCK inhibitor at a rate sufficient to create a steady state aqueous humor concentration of ROCK inhibitor of between about 0.002 μM to about 0.3 μM for the prolonged period of time (e.g., as least one week, two weeks, three weeks, four weeks or longer).

In some embodiments, the implants exhibit a sustained release of a ROCK inhibitor at a rate sufficient to maintain an aqueous humor concentration of the ROCK inhibitor of between about 0.4 ng/mL and about 32,000 ng/mL for the prolonged period of time (e.g., as least one week, two weeks, three weeks, four weeks or longer). In another embodiment, the implants exhibit a sustained release of a ROCK inhibitor at a rate sufficient to maintain an aqueous humor concentration of the ROCK inhibitor of between about 1.0 ng/mL and about 100 ng/mL for the prolonged period of time (e.g., as least one week, two weeks, three weeks, four weeks or longer). The required rate of release from the implant can be estimated based on the aqueous humor turnover and desired concentrations. Assuming an aqueous humor turnover of 2.5% minute and an aqueous humor volume of 250 μL, the first order elimination rate constant would be k elim=0.6 hr −1 and t ½=1.15 hours. Using the relationship between desired steady state concentration and elimination rate constant, the release would equal the product of the desired aqueous humor ROCK concentration*k elim*aqueous humor volume. Hence, in some embodiments, the implants disclosed herein can be configured to deliver from about 1.4 ng/day to 115 μg/day for the prolonged period of time (e.g., as least one week, two weeks, three weeks, four weeks or longer). In another embodiment, the implants disclosed herein can be configured to deliver from about 3.6 ng/day to 1000 ng/day for the prolonged period of time (e.g., as least one week, two weeks, three weeks, four weeks or longer).

As further detailed below, various types of implants can be used, including non-resorbable implants and bioresorbable implants. Various types of ROCK inhibitors can also be used, including, but not limited to, isoquinoline, pyridine, pyrimidine, pyrrolopyridine, indazole, and pyrazole based ROCK inhibitors, their derivatives, prodrugs, salts, and/or co-crystals. In some embodiments, the ROCK inhibitor is selected from at least one of netarsudil, Y-27632, H-1337, ripasudil, or fasudil. Other ROCK inhibitors can also be used.

In some embodiments, the implants disclosed herein can be configured to release the ROCK inhibitors over a prolonged period of time. For instance, in certain embodiments, the implant is configured to release ROCK inhibitors over a period of at least one week, two weeks, three weeks, four weeks, or longer after implantation in an eye of a patient. In other embodiments, the implant releases the ROCK inhibitors for a period of at least one month, two months, three months, or six months after implantation in an eye of a subject.

In some embodiments, the implant may exhibit a burst release of the ROCK inhibitors that is less than about 40% (w/w) over an initial 24-hour period from implantation in an eye of a patient. In further embodiments, the implant may exhibit a burst release of the ROCK inhibitors that is less than about 10% (w/w) over an initial 24-hour period from implantation in an eye of a patient. In still further embodiments, the implant may exhibit a burst release of the ROCK inhibitors that is less than about 5% (w/w) over an initial 24-hour period from implantation in an eye of a patient.

The release rate of the ROCK inhibitors from the implant may also be substantially constant. For example, in some embodiments, the release rate of the ROCK inhibitors from the implant may be substantially constant over an initial one, two, or three-month period starting at the end of the burst release or lag phase of the ROCK inhibitor, but not more than 14 days after implantation or in vitro release studies. The lag phase may be defined as the period immediately post-implantation or immediately after initiating in vitro release studies where no drug is released or the drug is released at a slower rate than the constant rate achieved after not more than 30 days.

The release rate of the ROCK inhibitors from the implant may be near-zero order or pseudo-zero order. For example, in some embodiments, the release rate of the ROCK inhibitors from the implant may be near-zero order or pseudo-zero order over an initial one, two, or three-month period from implantation starting at the end of the burst release or lag phase of the ROCK inhibitor. Near-zero order release and pseudo-zero order release kinetics may be defined as an essentially linear relationship between the cumulative amount of ROCK inhibitor released from the implant in vivo or in vitro release studies as a function of time.

The components of the embodiments as generally described and illustrated in the figures herein can be arranged and designed in a wide variety of different configurations. Thus, the following more detailed description of various embodiments, as represented in the figures, is not intended to limit the scope of the present disclosure, but is merely representative of various embodiments. While various aspects of the embodiments are presented in drawings, the drawings are not necessarily drawn to scale unless specifically indicated.

FIGS. 1A-1C depict an intracameral implant 100 according to one embodiment of the present disclosure. More particularly, FIG. 1A depicts a perspective view of an implant 100; FIG. 1B depicts a perspective view of the implant 100 including a therapeutic composition 110 disposed thereon; and FIG. 1C depicts a cross-sectional view of the implant 100 and therapeutic composition 110 of FIG. 1B, taken along the view line 1C-1C.

As shown in FIG. 1A-1C, in some embodiments, the implant includes an anchor body 102 and a therapeutic composition 110 that are separate and distinct. The anchor body 102 can include a lower portion 104 and an upper portion 106. The lower portion 104 can be configured to anchor and/or attach the anchor body 102 to a patient after insertion and/or implantation. For instance, the lower portion 104 can include one or more barbs or projections to aid in anchoring and/or attaching the anchor body 102 in a patient's eye. The upper portion 106 can be configured to receive and/or retain a therapeutic composition 110. For instance, the upper portion 106 can include a center region having one or more projections to aid in retaining a therapeutic composition 110.

The anchor body 102 can include various materials, including, but not limited, to metallic materials, polymeric materials, composite materials, and combinations thereof. In certain embodiments, the anchor body 102 includes nitinol. Other materials can also be used.

In some embodiments, the anchor body 102 is non-bioresorbable. In other words, the anchor body 102 can be configured such that it does not biodegrade while disposed within the patient's eye over a prolonged period of time, such as for at least 6 months, at least 1 year, at least 2 years, at least 5 years, or indefinitely. In other embodiments, the anchor body 102 can be configured to biodegrade over a period of time.

The therapeutic composition 110 can be disposed on or otherwise affixed to the anchor body 102. The therapeutic composition 110 can include a carrier matrix and a therapeutic agent. When implanted in a patient's eye, the therapeutic agent is configured to be released. In some embodiments, the therapeutic composition 110 biodegrades to release the therapeutic agent. In further embodiments, an elution membrane 112 can be disposed over the therapeutic composition 110 to control the release of the therapeutic agent. In FIGS. 1B and 1C, for example, an elution membrane 112 is shown disposed over and encapsulating the therapeutic composition 110. The elution membrane 112 can control the release of the therapeutic agent. The elution membrane 112 can also aid in retaining the therapeutic agent on the anchor body 102.

Various types of elution membranes 112 can be used, including, but not limited to, polymeric materials such as poly (vinyl alcohol), poly methyl methacrylate, poly hydroxyethylmethacrylate polyurethanes such as Elasthane, polydimethylsiloxanes, Carbosil (a silicone polycarbonate urethane) and ethylene vinyl acetate (EVA). The elution membrane 112 can be configured such that it is semipermeable and allow for the controlled release of the therapeutic agent (e.g., ROCK inhibitor). The delivery system can be designed such that the therapeutic agent (e.g., ROCK inhibitor) can be placed in a reservoir covered by the membrane and diffuse through the membrane, the therapeutic agent can also be dispersed within the membrane and diffuse out from there or both. Further, the elution membrane 112 can be configured such that the release of the therapeutic agent (e.g., ROCK inhibitor) is substantially constant and/or reproducible. In some embodiments, the elution membrane 112 is configured to release the therapeutic agent at a rate of between about 1.4 ng/day to 115 µg/day for the prolonged period of time (e.g., as least one week, two weeks, three weeks, four weeks or longer). In other embodiments, the elution membrane 112 is configured to release the therapeutic agent at a rate of between about 3.6 ng/day to 1000 ng/day for the prolonged period of time (e.g., as least one week, two weeks, three weeks, four weeks or longer).

The therapeutic agent can include one or more ROCK inhibitors. Various types of ROCK inhibitors can also be used, including, but not limited to, isoquinoline, pyridine, pyrimidine, pyrrolopyridine, indazole, and pyrazole based ROCK inhibitors, their derivatives, prodrugs, salts, and/or co-crystals. In some embodiments, the ROCK inhibitor is selected from at least one of netarsudil, Y-27632, H-1337, ripasudil, or fasudil. Other ROCK inhibitors can also be used.

Various types of matrix materials can also be used in the therapeutic composition, including, but not limited to, various types of pharmaceutically acceptable carriers and/or excipients. The term "pharmaceutically acceptable," as used herein, means a substance that does not substantially interfere with the effectiveness or the biological activity of the active agent (or agents) and which is not toxic to the patient in the amounts used. The matrix can be a solution, semisolid, paste, gel, hydrogel or solid pellet. Examples of pharmaceutically acceptable carriers include sterile liquids, such as water and oils, including those of petroleum, animal, vegetable or synthetic origin, such as peanut oil, soybean oil, mineral oil, and sesame oil. Suitable pharmaceutical excipients include starch, glucose, lactose, sucrose, gelatin, malt, rice, flour, chalk, silica gel, sodium stearate, glycerol monostearate, talc, sodium chloride, dried skim milk, glycerol, propylene glycol, water, and ethanol. The composition, if desired, can also contain wetting or emulsifying agents, surfactants, glidants and lubricants, fillers, disintegrating agents, tonicity adjusters, and/or pH buffering agents. Additional excipients may include polymers such as poly lactic acid, poly (lactic-co-glycolic) acid, cellulosic polymers such as methylcellulose, hydroxypropyl methylcellulose, carboxymethylcellulose, ethyl cellulose, polycaprolactone, poly orthoesters, polyanhydrides, polyethylene glycol and polyvinylpyrrolidone, poly orthoesters, polyvinyl alcohol, block co-polymers of polyesters and polyethylene glycol or various polyesters and block co-polymers such as poloxamers and polyacrylic acids such as carbomers. The matrix can be comprised of the ROCK inhibitor dispersed within fatty alcohols, fatty acids and or triglycerides. Natural polymers such as gellan gum, xanthan gum, hyaluronic acid, gelatin, collagen, chitosan, alginate, pectin and their salts and crosslinked analogs can also be used as part of the matrix. Cyclodextrins may be included. Surfactants including pluronics F127 and F68, polysorbate 20 and polysorbate 80 can be incorporated. Rheology modifiers such as the semisynthetic cellulose derivatives or carbopols such as carbopol 940 or carbopol ultrez can also be incorporated if desired.

As previously discussed, the implant 100 can be configured for delivery into a patient, such as for delivery into a patient's eye. In certain embodiments, the implant 100 can be inserted and/or implanted into the patient's sclera. In some embodiments, the implant 100 can be inserted and/or implanted into the patient's anterior chamber angle. In particular embodiments, the implant 100 can be inserted and/or implanted into Schlemm's Canal. The implant 100 can also be inserted into other regions within the patient's eye. When implanted or otherwise disposed in the patient's eye, the implant 100 can be configured to deliver ROCK inhibitors directly to the intracameral space such that the therapeutic effect of the ROCK inhibitor is maintained over a prolonged period of time.

Figure 2B:
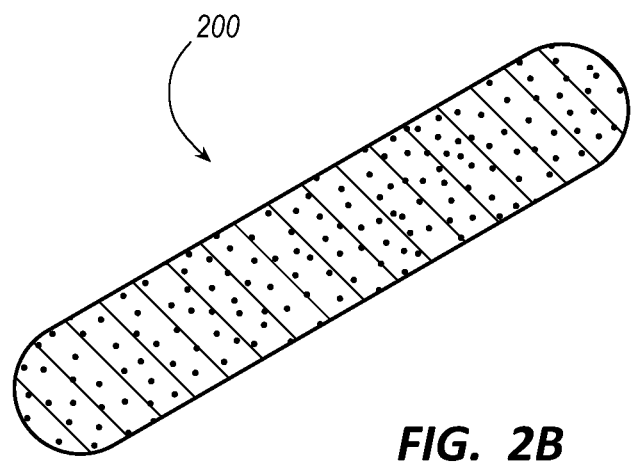
FIG. 2B is a cross-sectional view of the implant of FIG. 2A, taken along the view line 2B-2B.

FIGS. 2A and 2B depict an intracameral implant 200 according to another embodiment of the present disclosure. More particular, FIG. 2A depicts a perspective view of the implant 200; and FIG. 2B depicts a cross-sectional view of the implant 200 along the view line 2B-2B.

In the embodiment of FIGS. 2A-2B, the implant 200 is configured as a bioresorbable or biodegradable implant. In other words, the implant 200 is configured to biodegrade after implantation into a patient's eye. In some embodiments, the implant 200 includes a therapeutic composition that degrades over the course of hours, days, week, or months to sustain the release of the therapeutic agent. The residual polymer can further degrade shortly after the implant has released all the incorporated drug. In some embodiments, the time for degrading the implant 200 is less than 3 times the duration of efficacy, less than 2 times the duration of efficacy, or less than 1.5 times the duration of efficacy.

As disclosed above in relation to FIGS. 1A-1C, the therapeutic composition 110 can include a carrier matrix and a therapeutic agent. The therapeutic agent can be dispersed throughout the carrier matrix and/or implant 200 in a substantially homogenous manner. When implanted in a patient's eye, the therapeutic agent is configured to be released, such as when the therapeutic composition 110 and/or matrix material biodegrades within the patient's eye.

Any of the above identified matrix materials can be used in the therapeutic composition of 200. In certain embodiments, the matrix material comprises a polymeric material. Illustrative polymeric materials include, but are not limited to, poly lactic acid, poly (lactic-co-glycolic) acid, and combinations thereof. Other polymers that are suitable to form bioerodible matrix type delivery systems include, but are not limited to block co-polymers comprising polyesters, polycaprolactone, poly orthoesters, polyanhydrides. Natural and semisynthetic polysaccharides including salts of alginic acid and its salts, cellulosic polymers such as methyl cellulose, ethyl cellulose, hydroxypropyl methylcellulose, carboxymethyl cellulose and their salts, hyaluronic acid, and xanthan gum. Other polymers include polyvinyl alcohol, and poly ethylene vinyl acetate In some embodiments, the matrix includes poly (lactic-co-glycolic) acid having between about 20:80 and about 80:20 lactide to glycolide ratio. Other polymeric materials can also be used.

As discussed above, the therapeutic agent can also include one or more ROCK inhibitors. Various types of ROCK inhibitors can also be used, including, but not limited to, isoquinoline, pyridine, pyrimidine, pyrrolopyridine, indazole, and pyrazole based ROCK inhibitors, their derivatives, prodrugs, salts, and/or co-crystals. In some embodiments, the ROCK inhibitor is selected from at least one of netarsudil, Y-27632, H-1337, ripasudil, or fasudil. Other ROCK inhibitors can also be used.

The implants 200 can be formed in various ways. In some embodiments, the implant 200 can be formed by blending the polymeric material with the therapeutic agent. For example, in some embodiments, the therapeutic agent (e.g., ROCK inhibitor) is milled with one or more polymeric materials. In a particular embodiment, the therapeutic agent (e.g., ROCK inhibitor) is jet milled with or more polymeric materials. In such embodiments, the therapeutic agent (e.g., ROCK inhibitor) can be reduced to a consistent particle size. The therapeutic agent (e.g., ROCK inhibitor) and one or more polymeric materials can then be blended with a mixer to achieve a substantially homogeneous dispersion. The homogenous dispersion can then be formed into implants. For instance, the dispersion or mixture can be extruded into filaments by hot melt extrusion and cut into implants. Other methods of manufacture are also contemplated.

As previously discussed, the implant 200 can be configured for delivery into a patient, such as for delivery into a patient's eye. In certain embodiments, the implant 200 can be inserted and/or implanted into the patient's sclera. In some embodiments, the implant 200 can be inserted and/or implanted into the patient's anterior chamber angle. In particular embodiments, the implant 200 can be inserted and/or implanted into Schlemm's Canal. The implant 200 can also be inserted into other regions within the patient's eye. When implanted or otherwise disposed in the patient's eye, the implant 200 can be configured to deliver ROCK inhibitors directly to the intracameral space such that the therapeutic effect of the ROCK inhibitor is maintained over a prolonged period of time.

The present disclosure also provides methods related to the use of the implants disclosed herein. In certain embodiments, the present disclosure provides methods of introducing a ROCK inhibitor into an eye of a subject. Such methods comprise delivering an implant as described above into an eye of a subject. In other embodiments, the present disclosure provides methods of treating or preventing corneal disorders, diseases, and/or conditions, such as corneal endothelial dystrophies. The corneal disorders, diseases, and/or conditions (such as corneal endothelial dystrophies) can result from one or more of ocular surgery, cataract surgery, insertion of an implant, Fuch's corneal dystrophy, and failed descemetorhexis. Other methods are also contemplated.

EXAMPLES

To further illustrate these embodiments, the following examples are provided. These examples are not intended to limit the scope of the claimed invention, which should be determined solely on the basis of the attached claims.

Example 1

Non-resorbable implants were manufactured by affixing a therapeutic composition to a nitinol anchor body (e.g., similar to the embodiment discussed in relation to FIGS. 1A-1C). The therapeutic composition included the ROCK inhibitor netarsudil. An elution membrane including either Carbosil or EVA was used to encapsulate and affix the therapeutic composition to the nitinol anchor body. The elution membrane was semi-permeable to the ROCK inhibitor, allowing for controlled release of the ROCK inhibitor at a substantially reproducible rate. The Carbosil elution membrane was configured to elute the ROCK inhibitor at a rate of about 0.510 μg/day, and the EVA elution membrane was configured to elute the ROCK inhibitor at a rate of about 0.600 μg/day.

The in vivo pharmacokinetics of the ROCK inhibitor released from the implant was studied in Dutch Belted rabbits. Specifically, eight female Dutch Belted rabbits were administered an implant via a clear corneal incision at the superior temporal quadrant of the cornea and anchoring at the anterior chamber angle with either the implant made of Carbosil or EVA. Aqueous humor (AH) samples were tapped weekly and at study termination for analysis.

Intraocular implantation into the anterior chamber angle of rabbits with the implants made of Carbosil or EVA polymer resulted in ROCK inhibitor concentrations in the aqueous humor samples over the course of the 30 days. The aqueous humor concentrations are given in Table 1. At the end of the 30 day study the implants were explanted and the residual ROCK inhibitor amount was assayed. The residual amount of ROCK inhibitor left in the explants for both the Carbosil and EVA configurations was about 22.5% w/w. As shown therein, a sustained amount of ROCK inhibitor was present in each of the samples for the 30-day period.

TABLE 1

Netarsudil Concentrations

| Days | Netarsudil (ng/mL) in Aqueous Humor Samples Treated with Carbosil/Nitinol Implant | Netarsudil (ng/mL) in Aqueous Humor Samples Treated with EVA/Nitinol Implant |
|---|---|---|
| 7 | 1.52-2.57 | 1.16-5.06 |
| 14 | BLQ-3.53 | 1.11-5.34 |
| 21 | 2.03-2.33 | 2.39-5.33 |
| 28 | BLQ-14.9 | BLQ-3.88 |
| 30 | BLQ-4.68 | BLQ-1.44 |

BLQ = Below limit of quantitation;
N/A = Not Applicable

Example 2

Bioresorbable ROCK inhibitor implants can be made using polylactide-co-glycolide (PLGA) and poly lactic acid polymers (PLA). In doing so, polymers and blends of polymers can be mixed with the Rho Kinase inhibitor, extruded into filaments by hot melt extrusion, and cut into intracameral implants. Examples of polymers that can be used are given below in Table 2 and compositions in Table 3.

TABLE 2

Examples of PLA and PLGA Polymers

| Polymer Type | Inherent viscosity (dl/g) | Molecular Weight (kDa) | Glass Transition Temperature (° C.) | Ester End or Acid End | PLA or PLGA (lactide to glycolide ratio) |
|---|---|---|---|---|---|
| R203S | 0.25-0.35 | 18-28 | 46-50 | Ester End | PLA |
| R202S | 0.16-0.24 | 10-18 | 38-42 | Ester End | PLA |
| RG756S | 0.71-1.0 | 76-115 | 49-55 | Ester End | PLGA 75:25 |
| RG752H | 0.14-0.22 | 4-15 | 42-46 | Acid End | PLGA 75:25 |
| RG503 | 0.32-0.44 | 24-38 | 44-48 | Ester End | PLGA 50:50 |
| RG502 | 0.16-0.24 | 7-17 | 42-46 | Ester End | PLGA 50:50 |
| RG753S | 0.32-0.44 | | | | PLGA 75:25 |
| RG505 | 0.61-0.74 | 54-69 | 48-52 | Ester End | PLGA 50:50 |

TABLE 3

Composition Design Matrix (PLA, PLGA, and blends). (weights of polymers are in mg)

| # | 202S | 203S | 502 | 503 | 752H | 756S | Rho Kinase Inhibitor | Total (mg) |
|---|------|------|-----|-----|------|------|----------------------|------------|
| 1 | 80 | | | | | | 120 | 200 |
| 2 | | 80 | | | | | 120 | 200 |
| 3 | | | 80 | | | | 120 | 200 |
| 4 | | | | 80 | | | 120 | 200 |
| 5 | | | | | 80 | | 120 | 200 |
| 6 | | | | | | 80 | 120 | 200 |
| 7 | | 40 | | | | 40 | 120 | 200 |
| 8 | 40 | | | | | 40 | 120 | 200 |
| 9 | | 40 | 40 | | | | 120 | 200 |
| 10 | | 40 | | | 40 | | 120 | 200 |
| Total (mg) | 120 | 200 | 80 | 120 | 120 | 160 | 1200 | 2000 |

The compositions can be manufactured by milling the ROCK inhibitor and the PLA and PLGA polymers, such as with a jet mill. This allows for consistent particle size reduction of the starting materials. The polymers can then be mixed with the ROCK inhibitor according to the matrix in Table 3. Each mixture can be blended using a turbula mixer to achieve a homogeneous dispersion. Once mixed, the compositions can be extruded with a hot melt extruder.

Release of the ROCK inhibitor from the implants can be assessed in vitro. Implants can be placed into 50 mL polypropylene vials containing 45 mL of isotonic saline at pH 7.4 as the release media. The vials can then be placed on a shaker bath to agitate the medium at 37° C. At predetermined timepoints, the media can be sampled, and the entire receiver media replaced with fresh saline. The ROCK inhibitor concentration in the sampled aliquot can be quantified by High Performance Liquid Chromatography (HPLC), such as with a Waters Alliance e2695 system with a C-18 Hypersil ODS column. The ROCK inhibitor concentrations can be used to define the cumulative in vitro release of the compound from the implant as well as the daily ROCK inhibitor release rate.

Any methods disclosed herein include one or more steps or actions for performing the described method. The method steps and/or actions may be interchanged with one another. In other words, unless a specific order of steps or actions is required for proper operation of the embodiment, the order and/or use of specific steps and/or actions may be modified. Moreover, sub-routines or only a portion of a method described herein may be a separate method within the scope of this disclosure. Stated otherwise, some methods may include only a portion of the steps described in a more detailed method.

Recitation in the claims of the term "first" with respect to a feature or element does not necessarily imply the existence of a second or additional such feature or element. It will be apparent to those having skill in the art that changes may be made to the details of the above-described embodiments without departing from the underlying principles of the present disclosure.

Reference throughout this specification to "an embodiment" or "the embodiment" means that a particular feature, structure, or characteristic described in connection with that embodiment is included in at least one embodiment. Thus, the quoted phrases, or variations thereof, as recited throughout this specification are not necessarily all referring to the same embodiment.

Similarly, in the above description of embodiments, various features are sometimes grouped together in a single embodiment, figure, or description thereof for the purpose of streamlining the disclosure. This method of disclosure, however, is not to be interpreted as reflecting an intention that any claim require more features than those expressly recited in that claim. Rather, as the following claims reflect, inventive aspects lie in a combination of fewer than all features of any single foregoing disclosed embodiment.

The claims following this written disclosure are hereby expressly incorporated into the present written disclosure, with each claim standing on its own as a separate embodiment. This disclosure includes all permutations of the independent claims with their dependent claims. Moreover, additional embodiments capable of derivation from the independent and dependent claims that follow are also expressly incorporated into the present written description.

We claim:

1. An intracameral implant, comprising:
   a non-bioresorbable anchor,
   a Rho kinase (ROCK) inhibitor dispersed in a therapeutic composition disposed on the non-bioresorbable anchor, and
   an elution membrane that encapsulates the therapeutic composition, wherein the elution membrane is semipermeable to the ROCK inhibitor and controls a rate of release of the ROCK inhibitor,
   wherein the implant is configured to be disposed in an eye of a patient such that the implant is configured to release the ROCK inhibitor into an aqueous humor for sustained delivery of the ROCK inhibitor to the patient for a period of at least two weeks.

2. The intracameral implant of claim 1, wherein the implant is configured to release the ROCK inhibitor such that the aqueous humor concentration of the ROCK inhibitor is between about 0.001 µM and about 100 µM for the period of at least two weeks.

3. The intracameral implant of claim 1, wherein the implant is configured to release the ROCK inhibitor such that the aqueous humor concentration of the ROCK inhibitor is between about 0.4 ng/mL and about 32,000 ng/mL for the period of at least two weeks.

4. The intracameral implant of claim 1, wherein the implant is configured to release the ROCK inhibitor at a rate of between about 1 ng/day and about 115 µg/day for the period of at least two weeks.

5. The intracameral implant of claim 1, wherein the ROCK inhibitor is selected from at least one of netarsudil, Y-27632, H-1337, ripasudil, or fasudil.

6. The intracameral implant of claim 1, wherein the ROCK inhibitor comprises at least one of isoquinoline based ROCK inhibitors, pyridine based ROCK inhibitors, pyrimidine based ROCK inhibitors, pyrrolopyridine based ROCK inhibitors, indazole based ROCK inhibitors, or pyrazole based ROCK inhibitors, derivatives thereof, prodrugs thereof, salts thereof, and/or co-crystals thereof.

7. The intracameral implant of claim 1, wherein the elution membrane comprises a silicone polycarbonate urethane or ethylene vinyl acetate (EVA).

8. The intracameral implant of claim 1, wherein the implant is configured to treat a corneal endothelial dystrophy.

9. A method of treating a corneal endothelial dystrophy, comprising: disposing an intracameral implant of claim 1 into an eye of a patient, wherein the implant comprises a Rho kinase (ROCK) inhibitor and is configured to release the ROCK inhibitor into the eye of the patient for a period of at least two weeks.

10. The method of claim 9, wherein the implant is configured to release the ROCK inhibitor into the eye of the patient such that the aqueous humor concentration of the ROCK inhibitor is between about 0.001 µM and about 100 µM for the period of at least two weeks.

11. The method of claim 9, wherein the implant is configured to release the ROCK inhibitor into the eye of the patient such that the aqueous humor concentration of the ROCK inhibitor is between about 0.4 ng/ml and about 32,000 ng/mL for the period of at least two weeks.

12. The method of claim 9, wherein the implant is configured to release the ROCK inhibitor at a rate of between about 1 ng/day and about 115 µg/day for the period of at least two weeks.

* * * * *